United States Patent
Chung et al.

(10) Patent No.: US 11,957,697 B2
(45) Date of Patent: Apr. 16, 2024

(54) VIRAL RECEPTOR BOUND WITH SIALIC ACID COMPOUNDS

(71) Applicant: MVRIX CO., LTD., Hwaseong-si (KR)

(72) Inventors: Woo Jae Chung, Seoul (KR); Dae Hyuk Kweon, Seoul (KR); Jinhyo Chung, Suwon-si (KR); Caleb Hong, Chuncheon-si (KR)

(73) Assignee: MVRIX CO., LTD., Hwaseong-si (KR)

( * ) Notice: Subject to any disclaimer, the term of this patent is extended or adjusted under 35 U.S.C. 154(b) by 157 days.

(21) Appl. No.: 17/478,185

(22) Filed: Sep. 17, 2021

(65) Prior Publication Data
US 2022/0088046 A1 Mar. 24, 2022

(30) Foreign Application Priority Data
Sep. 18, 2020 (KR) .......... 10-2020-0120340

(51) Int. Cl.
*A61K 31/7012* (2006.01)
*A61K 47/54* (2017.01)
*A61P 31/12* (2006.01)

(52) U.S. Cl.
CPC ........ *A61K 31/7012* (2013.01); *A61K 47/542* (2017.08); *A61K 47/544* (2017.08); *A61K 47/549* (2017.08); *A61P 31/12* (2018.01)

(58) Field of Classification Search
CPC .............. A61K 31/7012; A61K 47/542; A61K 47/544; A61K 47/549; A61P 31/12
USPC ......................................................... 514/62
See application file for complete search history.

(56) References Cited

U.S. PATENT DOCUMENTS

2010/0068260 A1* 3/2010 Kruse .................. A61K 38/55
601/3

FOREIGN PATENT DOCUMENTS

| KR | 10-2018-0008338 A | 1/2018 |
| KR | 10-2018-0085689 A | 7/2018 |
| KR | 10-2065575 B1 | 1/2020 |
| KR | 10-2150980 B1 | 9/2020 |
| KR | 10-2181991 B1 | 11/2020 |
| KR | 10-2265446 B1 | 6/2021 |
| KR | 10-2021-0101792 A | 8/2021 |
| WO | WO 2009/002993 | * 12/2008 |

OTHER PUBLICATIONS

Hendricks et al. Sialylneolacto-N-tetraose c (LSTc)-bearing Liposomal Decoys Capture Influenza A Virus. The Journal of Biological Chemistry vol. 288, No. 12, pp. 8061-8073, Mar. 22, 2013. (Year: 2013).*

Chung, Jinhyo, et al., "Filamentous anti-influenza agents wrapping around viruses", Journal of Colloid and Interface Science 583 (2021) pp. 267-278.

* cited by examiner

*Primary Examiner* — Yih-Horng Shiao
(74) *Attorney, Agent, or Firm* — Sughrue Mion, PLLC

(57) ABSTRACT

Disclosed is a viral receptor that contains a sialic acid compound at one side thereof to provide binding affinity to a virus, and contains a lipid at the other side thereof, and that can be widely used for the treatment of viral infections based on this characteristic.

9 Claims, 20 Drawing Sheets

FIG. 2

VIRAL RECEPTOR BOUND WITH SIALIC ACID COMPOUNDS

BACKGROUND OF THE INVENTION

Field of the Invention

The present invention relates to a viral receptor bound with sialic acid compounds and to the use of the viral receptor.

Description of the Related Art

Viruses live in a manner dependent on living cells of organisms, thus causing various diseases. Typical diseases caused by viruses include AIDS, influenza, hepatitis, liver cancer, cervical cancer, tumors, hemorrhagic fever, respiratory diseases, food poisoning, pneumonia and the like.

Therapeutic agents for viral infections developed and known to date include amantadine- and rimantadine-based M2 ion channel inhibitors, oseltamivir (Tamiflu®), and zanamivir (Relenza®)-based neuraminidase inhibitors, but these therapeutic agents have a problem of limited efficacy. That is, it is known that amantadine or rimantadine-based derivative compounds rapidly lead to resistant variant viruses, and in some areas, H5N1-type influenza virus is known to be resistant to amantadine- or rimantadine-based compounds, and influenza B virus is known to be insensitive to amantadine derivatives. In addition, viruses resistant to oseltamivir- or zanamivir-based derivative compounds are also increasing.

Therefore, there is a need for various virus treatment methods that can solve the above-described virus resistance problem.

RELATED ART

Patent Literature

Korean Patent Laid-open Publication No. 10-2021-0101792 (publication date: Aug. 19, 2021) discloses that influenza virus can be captured with magnetic beads, the surface of which is coated with a sialic-acid/galactose complex.

Korean Patent No. 10-2065575 (publication date: Jan. 7, 2020) discloses that a conjugate containing sialic acid, sialyllactose, or a derivative thereof can bind to hemagglutinin present on the surface of the virus to thereby inhibit a viral infection process.

SUMMARY OF THE INVENTION

Therefore, the present invention has been made in view of the above problems, and it is an object of the present invention to develop a viral receptor having excellent virus-binding affinity and to provide the use of the viral receptor.

In accordance with a first aspect of the present invention, provided is a viral receptor containing a sialic acid compound and a spacer bound to each other, wherein the sialic acid compound contains sialic acid bound with galactose and glucose, and the spacer is a polymer having an amine group ($-NH_2$) or an aminooxy group ($NH_2-O-$) at one end thereof and a functional group capable of binding to a lipid at a remaining end thereof.

In the first aspect, the functional group capable of binding to the lipid is preferably a thiol group ($-SH$).

In the first aspect, any one lipid selected from phospholipid and fatty acid is preferably bound to the spacer.

In accordance with a second aspect of the present invention, provided is a viral receptor containing a sialic acid compound and a spacer bound to each other, wherein the sialic acid compound contains sialic acid bound with galactose and glucose, and the spacer is a polymer having an amine group ($-NH_2$) or an aminooxy group ($NH_2-O-$) at one end thereof and a carboxyl group ($-COOH$) capable of binding to a lipid at a remaining end thereof.

In the second aspect, the viral receptor is preferably bound with an anchor, which is a compound that has a functional group capable of binding to the carboxyl ($-COOH$) end group of the spacer at one end thereof and a functional group capable of binding to the lipid at a remaining end thereof.

In the second aspect, the anchor preferably has a thiol group as the functional group capable of binding to the lipid.

In the second aspect, any one lipid selected from phospholipid and fatty acid is preferably bound to the anchor.

In the first and second aspects, a plurality of spacers including the spacer is bound to one another via lysine to form a spacer complex.

Meanwhile, a plurality of lysines including the lysine is preferably bound to one another to form a lysine complex.

In the first and second aspects, the sialic acid compound is preferably bound to the spacer by forming a secondary amine bond through reaction of an aldehyde group of the glucose in the sialic acid compound with the amine group of the spacer, or by forming an oxime bond through reaction of the aldehyde group of the glucose in the sialic acid compound with the aminooxy group ($NH_2-O-$) of the spacer.

In the first and second aspects, the sialic acid compound preferably contains sialic acid bound with an oligosaccharide including a plurality of repeating units, each including a disaccharide in which galactose is combined with glucose.

In the first and second aspects, the sialic acid compound is preferably sialyllactose.

The sialyllactose is preferably 3'-sialyllactose or 6'-sialyllactose.

The lipid preferably has any one functional group selected from a maleimide group ($H_2C_2(CO)_2N-$), a pyridyl disulfide group ($Py-S-S-$), a haloacetyl group ($X-CH_2-CO-$), an acryloyl group ($H_2C=CH-CO-$), and a vinyl group ($H_2C=CR-$).

BRIEF DESCRIPTION OF THE DRAWINGS

The above and other objects, features and other advantages of the present invention will be more clearly understood from the following detailed description taken in conjunction with the accompanying drawings, in which:

FIG. 2 is a schematic diagram illustrating a process of synthesizing a single-stranded viral receptor (SL-M) and a multi-stranded viral receptor (SL-T) of the present invention;

DETAILED DESCRIPTION OF THE INVENTION

Figure 1:
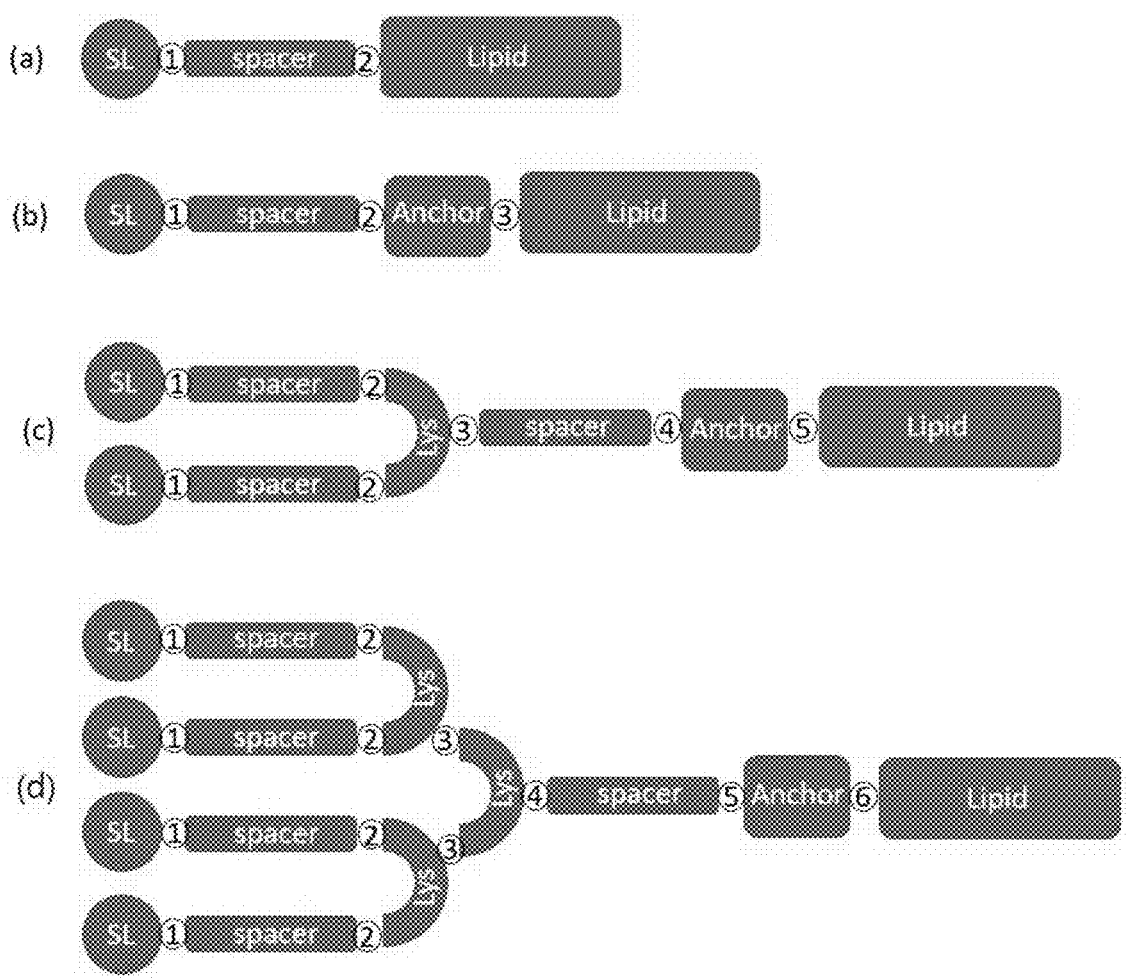
FIG. 1 is a schematic diagram for better understanding of the structure of the viral receptor of the present invention.

In a first aspect, the present invention provides a viral receptor containing a sialic acid compound and a spacer bound to each other, wherein the sialic acid compound contains sialic acid bound with galactose and glucose, and the spacer is a polymer having an amine group (—NH$_2$) or an aminooxy group (NH$_2$—O—) at one end thereof and a functional group capable of binding to a lipid at a remaining end thereof.

The experiment of the present invention demonstrated that the single-stranded viral receptor (SL-M) formed by binding the sialic acid compound to the spacer had virus-binding affinity, even though the spacer was bound to the sialic acid compound. That is, Example 13 demonstrated that the binding affinity for the virus surface protein (hemagglutinin) varies when the spacer is present and the length of the spacer is increased.

With regard to this aspect of the viral receptor of the present invention, the functional group capable of binding to the lipid is preferably be a thiol group (—SH). The thiol group can lead to a chemoselective reaction with high selectivity compared to other functional groups, and thus has the advantage of allowing a lipid to bind specifically to the desired position. The thiol group may bind to a lipid having a maleimide or pyridyl disulfide functional group to form a thiol bond.

In a second aspect, the present invention also provides a viral receptor containing a sialic acid compound and a spacer bound to each other, wherein the sialic acid compound contains sialic acid bound with galactose and glucose, and the spacer is a polymer having an amine group (—NH$_2$) or an aminooxy group (NH$_2$—O—) at one end thereof and a carboxyl group (—COOH) capable of binding to a lipid at a remaining end thereof.

The spacer used with regard to the second aspect of the present invention is a polymer capable of binding to the lipid, and has an amine group (—NH$_2$) or an aminooxy group (NH$_2$—O—) at one end thereof, and has a carboxyl group (—COOH) at the other end thereof. In addition, the lipid may be bound through the carboxyl group. Preferably, an anchor, which is a compound that has a functional group capable of binding to the carboxyl (—COOH) end group of the spacer on one end thereof and a functional group capable of binding to the lipid on the other end thereof, may be used for selective binding to the lipid. When an anchor is used, the anchor is interposed between the spacer and the lipid to bind the spacer to the lipid. The anchor is preferably cysteine.

Meanwhile, with respect to the anchor, the functional group capable of binding to the lipid, for example, includes any one selected from a thiol group (SH—), an azido group (N$_3$—), an alkynyl group (HC≡C—), and methyl ketone (CH$_3$CO—).

The thiol group may form a thioether bond with a maleimide (H$_2$C$_2$(CO)$_2$N—), haloacetyl (X—CH$_2$—CO—), acryloyl (H$_2$C=CH—CO—) or vinyl (H$_2$C=CR—) group of the lipid, or may form a disulfide bond with a pyridyl disulfide (Py-S—S—) group of the lipid. The azido group (N$_3$—) may form a triazole bond with the alkynyl group (HC≡C—) of the lipid. The alkynyl group (HC≡C—) may form a triazole bond with the azido group (N$_3$—) of the lipid. The methyl ketone group may form a hydrazide bond with a hydrazino group (NH$_2$—NH—) of the lipid.

Accordingly, the lipid bound to one end of the anchor preferably has any one functional group selected from alkynyl (HC≡C—), azido (N₃—), hydrazino (NH₂—NH—), maleimide (H₂C₂(CO)₂N—), haloacetyl (X—CH₂—CO—), acryloyl (H₂C═CH—CO—), vinyl (H₂C═CR—), and pyridyl disulfide (Py-SS—) groups in order to bind to the anchor.

Meanwhile, with regard to the first or second aspect of the viral receptor, any one lipid selected from a phospholipid or a fatty acid is preferably bound to the spacer.

The present invention is characterized in that the spacer is bound to the sialic acid compound and the lipid is bound to the spacer. In the present invention, the lipid serves to stably bind the viral receptor according to the present invention to a separate construct. That is, when the separate construct is, for example, micelles composed of phospholipids, liposomes, nanodiscs, or nanoperforators disclosed in Korean Patent No. 10-2181991 owned by the present inventors, the lipids present in the viral receptor of the present invention are intercalated between the phospholipids constituting the construct to form a hydrophobic bond with the phospholipids so that they can be stably positioned in the phospholipids. This enables the viral receptor of the present invention to be further stabilized structurally and to effectively perform the functions thereof in a viral therapeutic agent.

Meanwhile, with regard to the first or second aspect of the viral receptor, a plurality of spacers may be bound via lysine to form a spacer complex (see FIG. 1). This structure has an advantage in that two sialic acids can be bound to the unit viral receptor of the present invention.

This structure is possible because the lysine used in the present invention has alpha and epsilon amine functional groups at one end thereof and a carboxyl group at the other end thereof. For this reason, the alpha or epsilon amine group of lysine can form an amide bond with the carboxyl group of the spacer of the present invention (the spacer bound with the sialic acid compound). In addition, the carboxyl group of lysine may be bound to an amine group of another spacer to form an amide bond.

In addition, when two or more lysines are bound thereto in a branched form, a plurality of spacers (spacers bound with sialic acid compounds) may be bound thereto. The branched form of lysine can be produced by forming an amide bond between the amine group of one lysine and the carboxyl group of another lysine (see FIG. 1). This enables the spacer (the spacer bound with the sialic acid compound) to be formed in multiple strands. In this case, more sialic acids can be bound to the unit viral receptor of the present invention. The following examples experimentally demonstrated that a viral receptor formed as a quadruple layer has better virus-binding affinity than a viral receptor formed as a single layer.

Meanwhile, in the present invention, a sialic acid compound containing sialic acid bound with galactose and glucose is used. The sialic acid is preferably bound to galactose. In addition, a disaccharide in which galactose is combined with glucose is not limited to a specific form, but is preferably lactose. In addition, the sialic acid compound may be a compound in which sialic acid is bound with an oligosaccharide including a plurality of repeating units, each including a disaccharide (preferably lactose) in which galactose is combined with glucose.

Meanwhile, the sialic acid compound of the present invention is preferably sialyllactose. It is known that 3'-sialyllactose has high binding affinity for avian infection virus and that 6'-sialyllactose has high binding affinity for human infection virus. Accordingly, in the present invention, 3'-sialyllactose or 6'-sialyllactose may be selectively used, depending on the subject to which it is applied.

Therefore, the viral receptor of the present invention may be applied to any virus that can use a virus-binding affinity and examples thereof include viruses belonging to Bunyaviridae, Coronaviridae, Filoviridae, Flaviviridae, Hepadnaviridae, Herpesviridae, Orthomyxoviridae, Poxviridae, Rhabdoviridae, Retroviridae, Togaviridae, and Herpesviridae families. Other examples thereof include: Sin Nombre hantavirus, etc., which belongs to the Bunyaviridae family; coronavirus, etc., involved in various acute respiratory syndromes, which belongs to the Coronaviridae family; Ebola virus, Marburg virus, etc., which belong to the Filoviridae family; West Nile virus, yellow Fever virus, Dengue Fever virus, Hepatitis C virus, etc., which belong to the Flaviviridae family; hepatitis B virus, etc., which belongs to the Hepadnaviridae family; herpes simplex 1 virus, herpes simplex 2 virus, etc., which belong to the Hepadnaviridae family; influenza virus etc., which belongs to the Orthomyxoviridae family; smallpox virus, vaccinia virus, molluscum contagiosum virus, monkeypox virus, etc., which belong to the Poxviridae family; rabies virus, etc., which belongs to the Rhabdoviridae family; HIV (human immunodeficiency virus) etc., which belongs to the Retroviridae family; Chikungunya virus etc., which belongs to the Togaviridae family; and pseudorabies virus, HHV virus, etc., which belong to the Herpesviridae family.

Meanwhile, preferably, the sialic acid compound may be bound to the spacer by forming a secondary amine bond through reaction of the aldehyde group of the glucose in the sialic acid compound with the amine group of the spacer, or by forming an oxime bond through reaction of the aldehyde group of the glucose in the sialic acid compound with the aminooxy group (NH₂—O—) of the spacer.

Meanwhile, in the present invention, the spacer is preferably ethylene glycol or a polymer thereof, more preferably ethylene glycol having a length of 0.8 to 1.2 nm or a polymer thereof.

Hereinafter, the present invention will be described in more detail with reference to the following examples. The scope of the present invention is not limited to the examples, and encompasses modifications of the technical concept equivalent thereto.

Example 1: Synthesis of Single-Stranded Viral Receptor (SL-M) and Multi-Stranded Viral Receptor (SL-T)

(1) Introduction

In this embodiment, single-stranded viral receptors (SL-M) and multi-stranded viral receptors (SL-T) were synthesized using PEG (polyethylene glycol), i.e., 9-amino-4,7-dioxanonanoic acid having an amine group at one end thereof and a carboxyl group at the other end thereof as a spacer, and cysteine having a thiol group (PEG) as an anchor (the carboxyl group of PEG has the same reaction characteristics as the carboxyl group of sialyllactose and thus cannot form a selective bond, so an anchor having a thiol group capable of performing chemoselective reaction is used instead of the carboxyl group of PEG). That is, in this embodiment, a single-stranded viral receptor composed of "sialyllactose-PEG-cysteine" (hereinafter referred to as "SL-M") and a multi-stranded viral receptor composed of "(sialyllactose-PEG)₄-lysine₃-PEG(spacer)-cysteine" (hereinafter referred to as "SL-T") were synthesized. In this case, the aldehyde group of sialyllactose reacted with the amine group of PEG, followed by a reduction reaction to induce a secondary amine bond enabling linking between the aldehyde group and the amine group. In addition, the carboxyl group of PEG reacted with the amine group of cysteine to induce an amide bond enabling linking between the aldehyde group and the amine group.

Meanwhile, sialyllactose is classified into 3'-sialyllactose (3'-SL) and 6'-sialyllactose (6'-SL), which are determined depending on the position of the alcohol group of galactose that binds to sialic acid, each of which has different preferences depending on the type of influenza virus. Here, 3'-SL was used to determine the difference in affinity with various types of viruses and the inhibitory activity thereto.

Meanwhile, the multi-stranded viral receptor (SL-T) of this example was synthesized by further applying lysine to the method for producing a single-stranded viral receptor, and then the strand thereof was extended by adding epsilon amine thereto.

Figure 2:
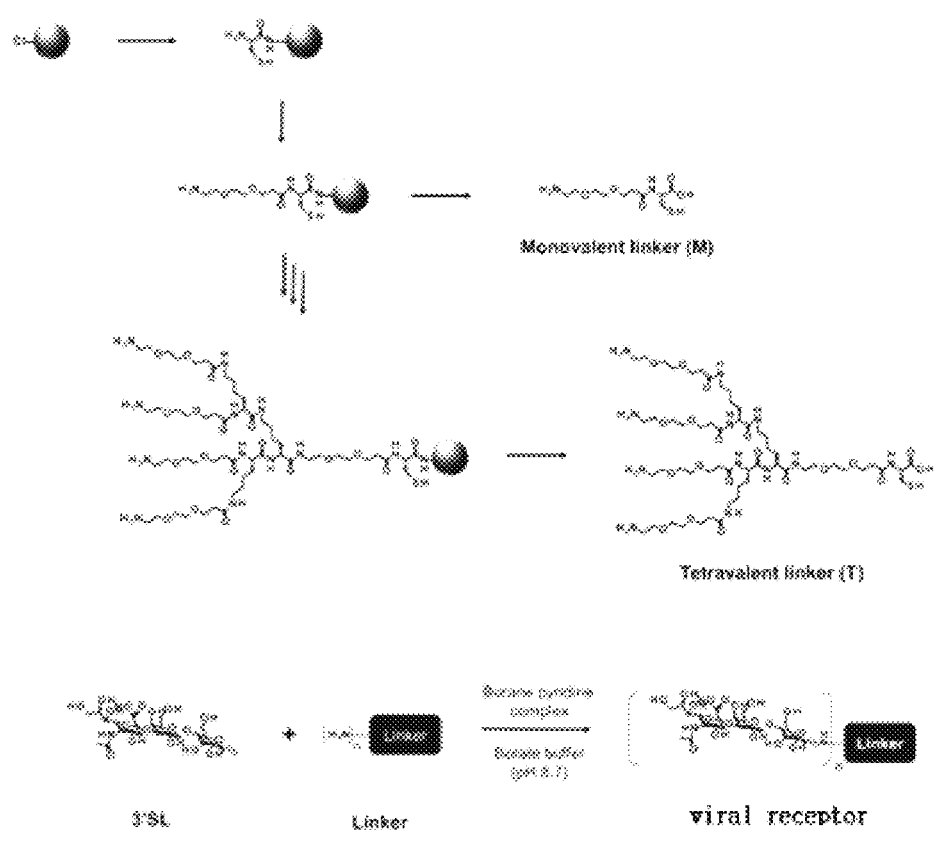

Meanwhile, the process according to this synthesis method is shown in FIG. 2.

2) Synthesis

The linker (hereinafter, the term "linker" refers to a viral receptor structure of the present invention to which sialyllactose and lipid are not bound, and which includes an anchor) was produced by a standard Fmoc-based solid-phase peptide synthesis method.

A 2-chlorotritylchloride (2-CTC) resin was swollen in a DCM (dichloromethane) solvent for 10 minutes. Then, Fmoc-Cys(Trt)-OH (3 eq.) and DIPEA (N,N-diisopropylethylamine) (3 eq.) were reacted with the 2-CTC resin in a DCM (dichloromethane) solvent at room temperature for 3 hours. Then, the unreacted functional groups of the resin were end-capped with methanol for 30 minutes. The Fmoc group was removed with a 25% (v/v) 4-methylpyperidine/NMP (N-methyl-2-pyrrolidone) solution for 30 minutes, and the resin was washed with DMF (dimethylformamide) (×2), DCM (×3), MeOH (×3), and DMF (×2).

The resin was reacted with 9-[(9H-fluoren-9-ylmethoxy) carbonylamino]-4,7-dioxanonanoic acid, DIC, and HOBt (each 3 eq.) in the presence of the NMP solvent at room temperature. After complete resin-phase synthesis, the single-stranded linker, the ADON-Cys linker was cleaved from the resin using a mixture of 82.5% TFA, 5% water, 5% phenol, 5% thioanisole and 2.5% 1,2-ethanedithiol at room temperature for 2 hours.

After removal of the solvent using a rotary evaporator, the crude product was precipitated with ice-cold diethyl ether (30 times in volume) and the crude product was collected via centrifugation to obtain a white solid. The linker was further purified to a purity higher than 95% (yield higher than 85%) by semi-preparative HPLC. Then, a single-stranded receptor was synthesized by binding 3'-sialyllactose or 6'-sialyllactose to a linker through reductive amination. The reductive amination was performed by reacting the single-stranded linker with sialyllactose (3 eq.) at 50° C. for 3 days under magnetic stirring (400 rpm) while adding NaCNBH$_3$ (1 eq.) to the reaction mixture in a pH 8.7 borate buffer solution once daily. Then, the resulting product was purified by semi-prep HPLC to obtain a single-stranded receptor (3'-SL-M or 6'-SL-M).

Example 2: Analysis of Single-Stranded Viral Receptor (SL-M) and Multi-Stranded Viral Receptor (SL-T)

1) ESI-MS Analysis

Figure 3:
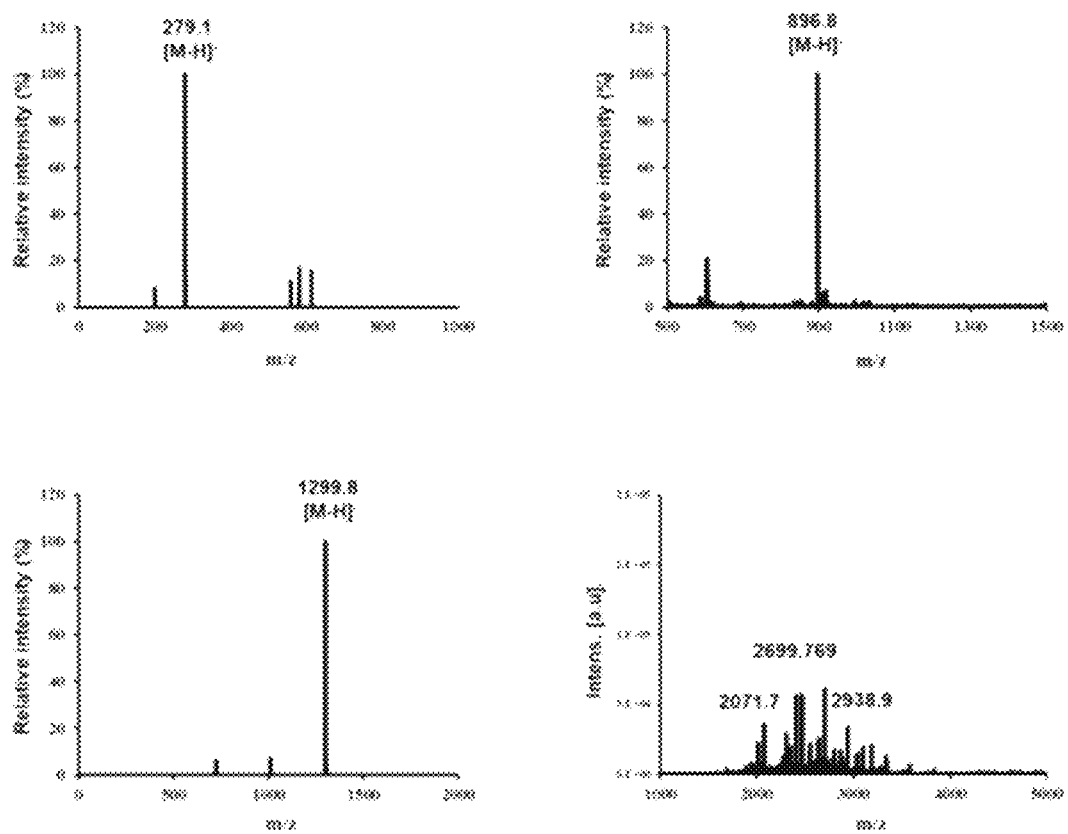
FIG. 3 illustrates the results of ESI MS analysis of the single-stranded linker, single-stranded viral receptor (SL-M), multi-stranded linker and multi-stranded viral receptor (SL-T) of the present invention.

The results of synthesis of linkers and viral receptors were observed through ESI MS analysis (FIG. 3).

FIG. 3 illustrates the results of ESI MS analysis of a) a single-stranded linker, b) a single-stranded viral receptor (SL-M, linker bound with sialyllactose), c) a multi-stranded linker, and d) a multi-stranded viral receptor (SL-T, linker bound with sialyllactose).

Compared to the single-stranded linker bound with 3'-sialyllactose, the multi-stranded linker bound with 3'-sialyllactose exhibited a greater increase in molecular weight, which means that more 3'-sialyllactose was bound to the multi-stranded linker than to the single-stranded linker.

2) H-NMR Analysis $^1$H-NMR spectral analysis was performed for single- and multi-stranded viral receptors. $^1$H-NMR spectral analysis was performed at 700 MHz NMR on a sample dissolved in a deuterium oxide (DO) solvent (FIGS. 4 and 5).

Figure 4:
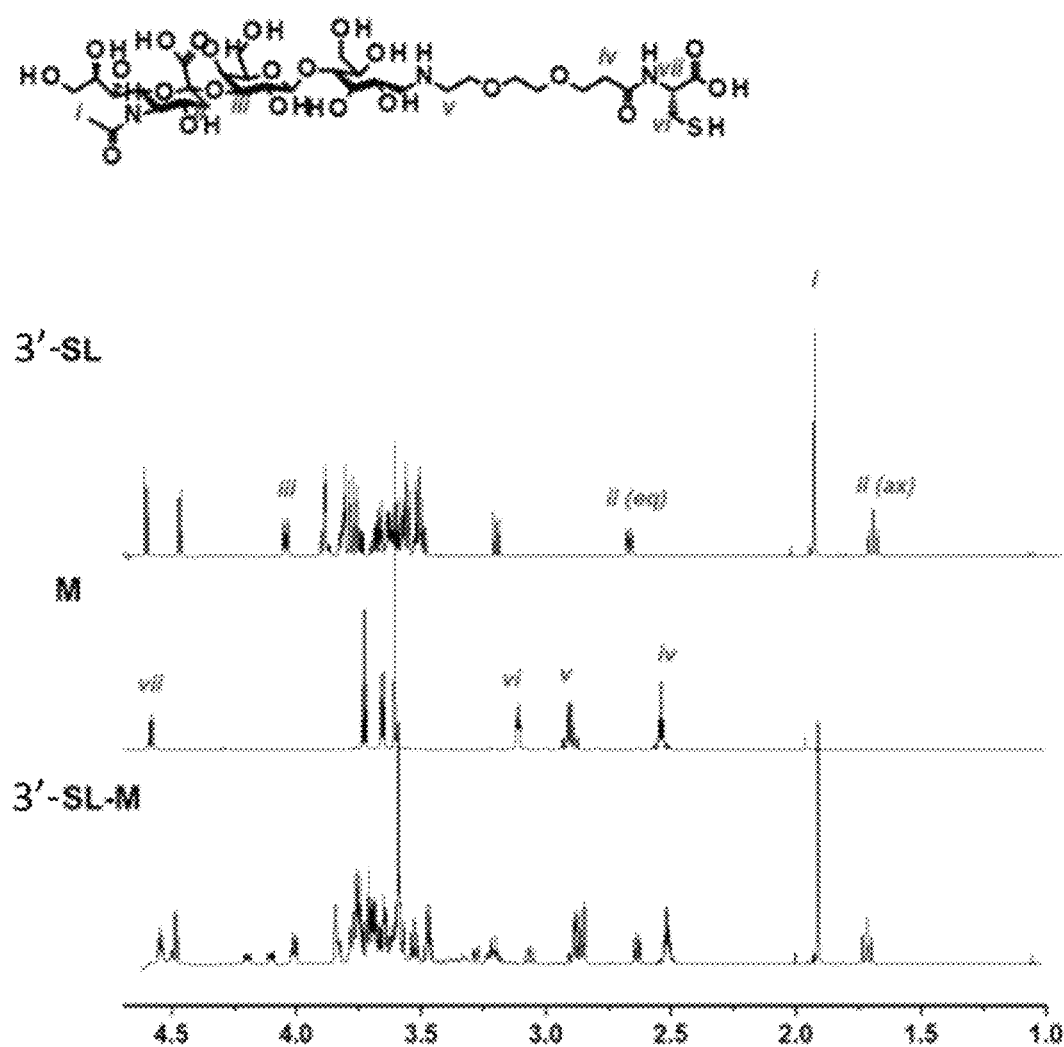
FIG. 4 illustrates the result of $^1$H-NMR analysis of the single-stranded viral receptor (SL-M) of the present invention.
Figure 5:
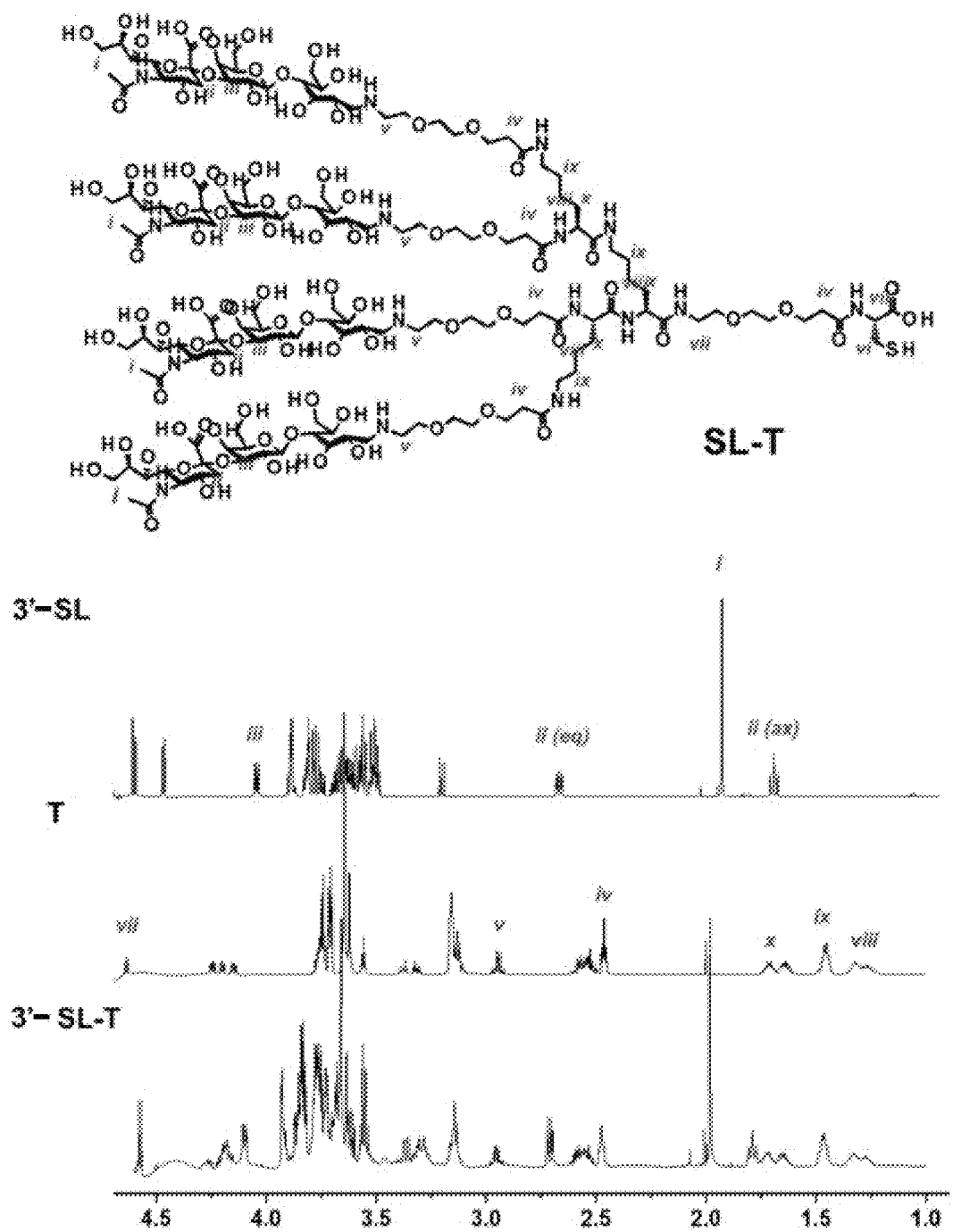
FIG. 5 illustrates the result of $^1$H-NMR analysis of the multi-stranded viral receptor (SL-T) of the present invention.

FIG. 4 is an NMR spectrum of a single-stranded viral receptor (3'-SL-M) bound with 3'-sialyllactose and FIG. 5 is an NMR spectrum of a multi-stranded viral receptor (3'-SL-T) bound with 3'-sialyllactose.

Based on the results of H-NMR spectral analysis, 1.45 ppm of the delta carbon of the linker was compared with 2.07 ppm of the acetyl group of SL (sialyllactose) to calculate the amount of SL that was bound to the linker. This demonstrated that the 3'-SL-bound single-stranded viral receptor (3'-SL-T) had almost completely quantitatively sialyllactose bound to 100% of the amine group, and the 3'-SL-bound multi-stranded viral receptor (3'-SL-M) had sialyllactose bound to about 97.5% of the amine group.

Figure 6:
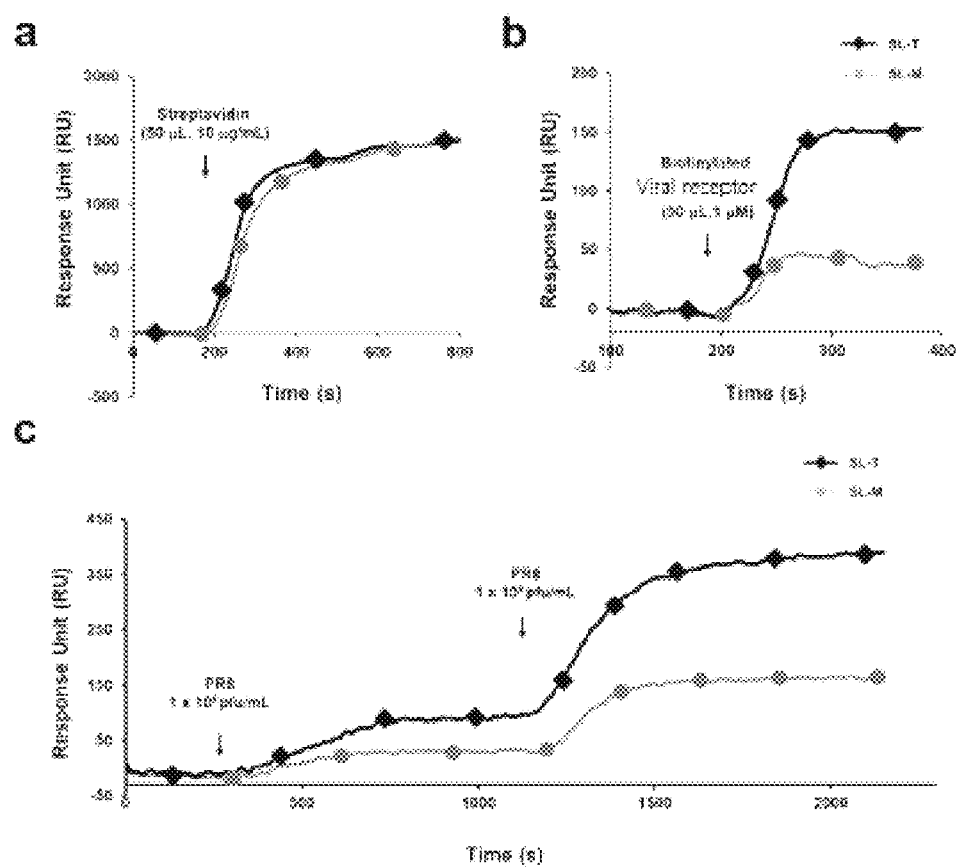
FIG. 6 illustrates the result of surface plasmon resonance (SPR) analysis to determine the virus affinity of the single-stranded viral receptor (SL-M) and the multi-stranded viral receptor (SL-T) of the present invention.

Example 3: Analysis of Virus-Binding Affinity of Single-Stranded and Multi-Stranded Viral Receptors First, maleimide-PEG2-biotin was bound to the cysteine end of each viral receptor (3'-SL-M, 3'-SL-T) to introduce biotin therein. For SPR analysis, streptavidin was immobilized on a gold chip (FIG. 6A), and 3'-SL-M-biotin and 3'-SL-T-biotin solutions (in a phosphate buffer having a pH of 7.4) were poured thereon to introduce a single-stranded viral receptor (3'-SL-M) and a multi-stranded viral receptor (3'-SL-T) onto the surface (FIG. 6B). Then, the surface of the immobilized single-stranded viral receptor (3'-SL-M) and multi-stranded viral receptor (3'-SL-T) was treated with the same concentration of PR8 (Puerto Rico/8 H1N1) virus. Both the immobilized single-stranded viral receptor (3'-SL-M) and the multi-stranded viral receptor (3'-SL-T) had virus-binding affinity, and the measured binding affinity of the multi-stranded viral receptor (3'-SL-T) was about three times higher than that of the single-stranded viral receptor (3'-SL-M) (FIG. 6C).

Example 4: Synthesis of Single-Stranded Viral Receptor and Nanodisc Using Disulfide Bond The nanodisc used in this example was prepared in accordance with a method disclosed in Korean Patent No. 2181991 using PDP-PE (1,2-dioleoyl-sn-glycero-3-phosphoethanolamine-N-[3-(2-pyridyldithio)propionate]) as one of the phospholipid components (using PDP-PE instead of ⅕-mol of POPC (1-palmitoyl-2-oleoyl-sn-glycero-3-phosphocholine) used in Korean Patent No. 10-2181991).

Figure 7:
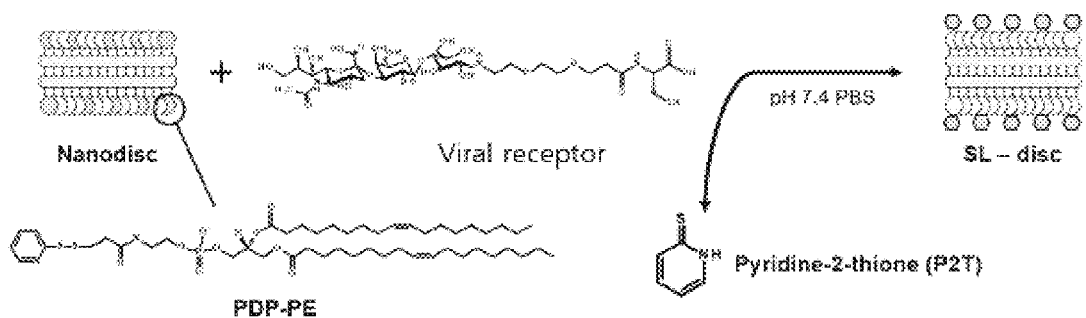
FIG. 7 illustrates a process of binding the single-stranded viral receptor (SL-M) of the present invention to a nanodisc.

This nanodisc used PDP-PE (1,2-dioleoyl-sn-glycero-3-phosphoethanolamine-N-[3-(2-pyridyldithio)propionate]) as one of the phospholipid components. The pyridyl disulfide functional group reacts with a thiol group present in the single-stranded viral receptor (SL-M) in a pH 7.4 phosphate buffer saline without a catalyst to form a disulfide bond. As described above, a lipid is bound to a single-stranded viral receptor to form a viral receptor lipid (hereinafter, the term "viral receptor lipid" refers to a A schematic diagram of this reaction is shown in FIG. 7. The single-stranded viral receptors used herein were a single-stranded viral receptor bound with 3'-SL and a single-stranded viral receptor bound with 6'-SL.

Figure 8:
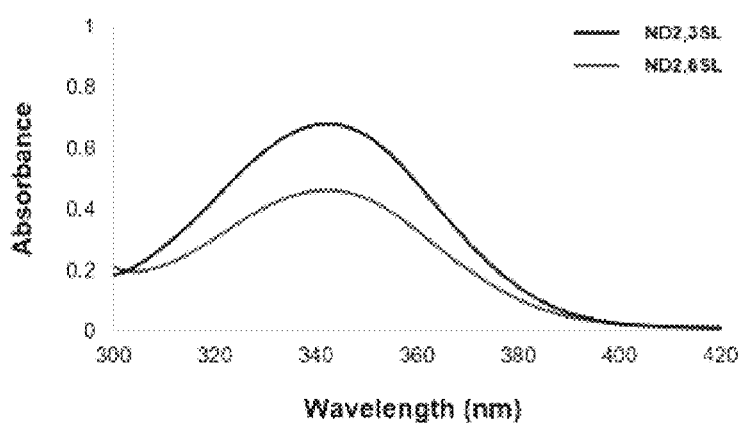
FIG. 8 illustrates absorbance measured to calculate the ratio of lipids having a single-stranded receptor to total lipids contained in a nanodisc synthesized using pyridine-2-thione (P2T), which is a byproduct of the binding between the single-stranded viral receptor (SL-M) of the present invention and the nanodisc.

The byproduct of the disulfide bond reaction, pyridine-2-thione (P2T), has absorbance at 342 nm. The measured absorbance enables calculation of the ratio of the lipid having the single-stranded viral receptor to the total lipid contained in the nanodisc (FIG. 8).

The result of calculation showed that the nanodisc (ND2, 3'-SL) having a 3'-SL single-stranded viral receptor was bound to 44% of the PDP-PE present in the nanodisc, and the nanodisc (ND2,6'-SL) having a 6'-SL single-stranded viral receptor was bound to 41.5% of the PDP-PE present in the nanodisc.

Figure 9:
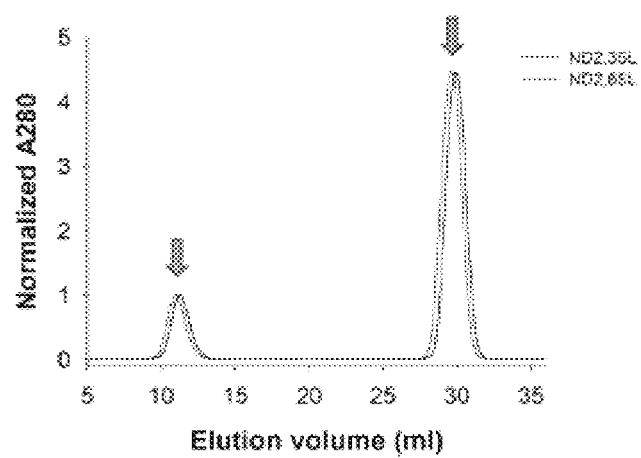
FIG. 9 illustrates separation of a binding product by FPLC (fast protein liquid chromatography) after binding of the single-stranded viral receptor (SL-M) of the present invention to the nanodisc.

Then, pyridine-2-thione (P2T) was removed through FPLC (hast protein liquid chromatography) to obtain intact single-stranded viral receptor-bound nanodiscs (ND2,6'-SL and ND2,3'-SL) (FIG. 9).

In FIG. 9, "elution volume 12 mL" means nanodiscs (ND2,6'-SL; ND2,3'-SL) synthesized from a single-stranded viral receptor, and "elution volume 30 mL" means pyridine-2-thione (P2T).

Example 5: Experiment on Antiviral Efficacy of Nanodiscs (ND2,6'-SL; ND2,3'-SL) Bound with Viral Receptor Lipid of Present Invention in which Lipid is Bound to Single-Stranded Viral Receptor (SL-T)

Conventional nanoperforators using ganglioside as a receptor have a problem in that they do not have anti-influenza effects on some strains of influenza virus. Whether or not this problem could be solved when sialyllactose was used as a receptor was determined.

Figure 10:
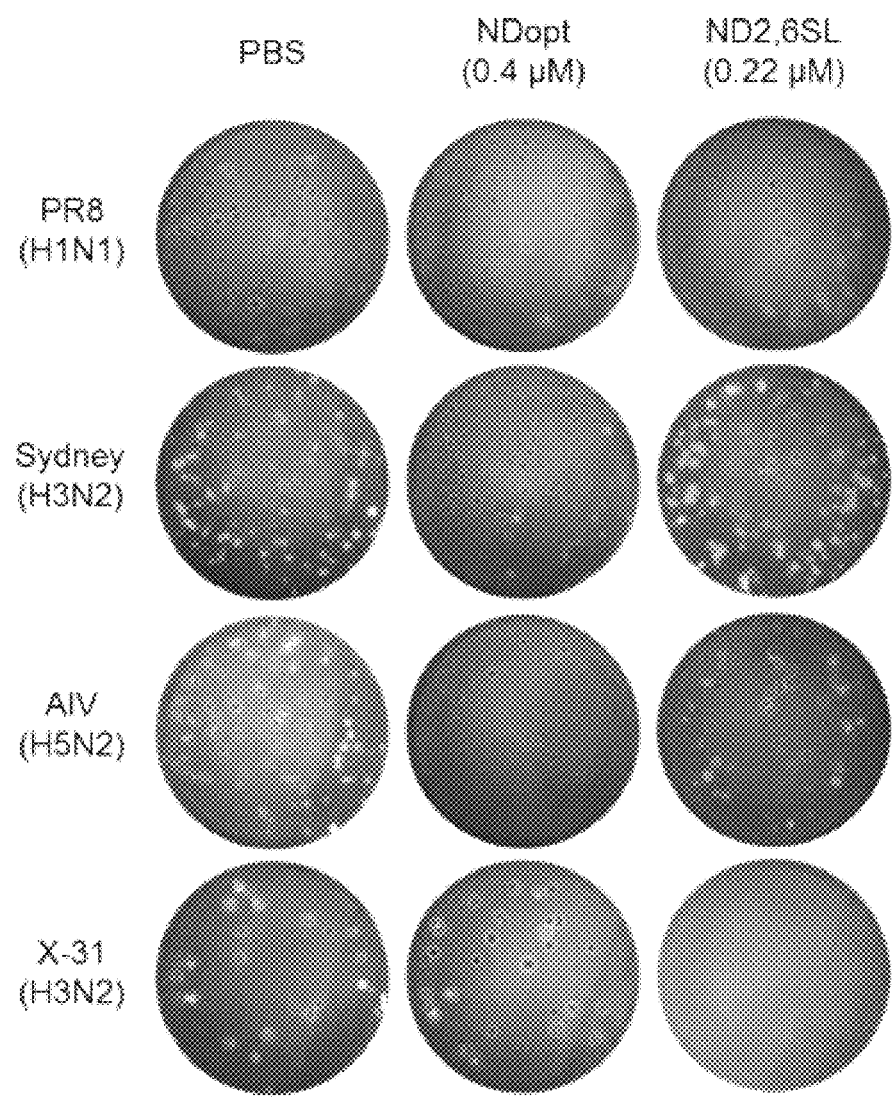
FIG. 10 illustrates the result of treating the virus with the nanodisc (ND2,3SL) bound with the single-stranded viral receptor according to the present invention.

For this purpose, a plaque reduction assay [essay for analyzing the extent to which a cell lesion effect (plaque formation caused by virus) is inhibited] was performed using the nanodiscs (ND2,6'-SL; ND2,3'-SL) bound with the viral receptor lipid of the present invention in which a lipid is bound to a single-stranded viral receptor (SL-T), and the viruses PR8 (H1N1), Sydney (H3N2), AIV (H5N2), and X-31 (H3N2). The result of the experiment showed that ND2,6'-SL' had antiviral activity to the X-31 strain, on which the conventional nanoperforator using ganglioside as a receptor had no effect (FIG. 10).

Figure 11:
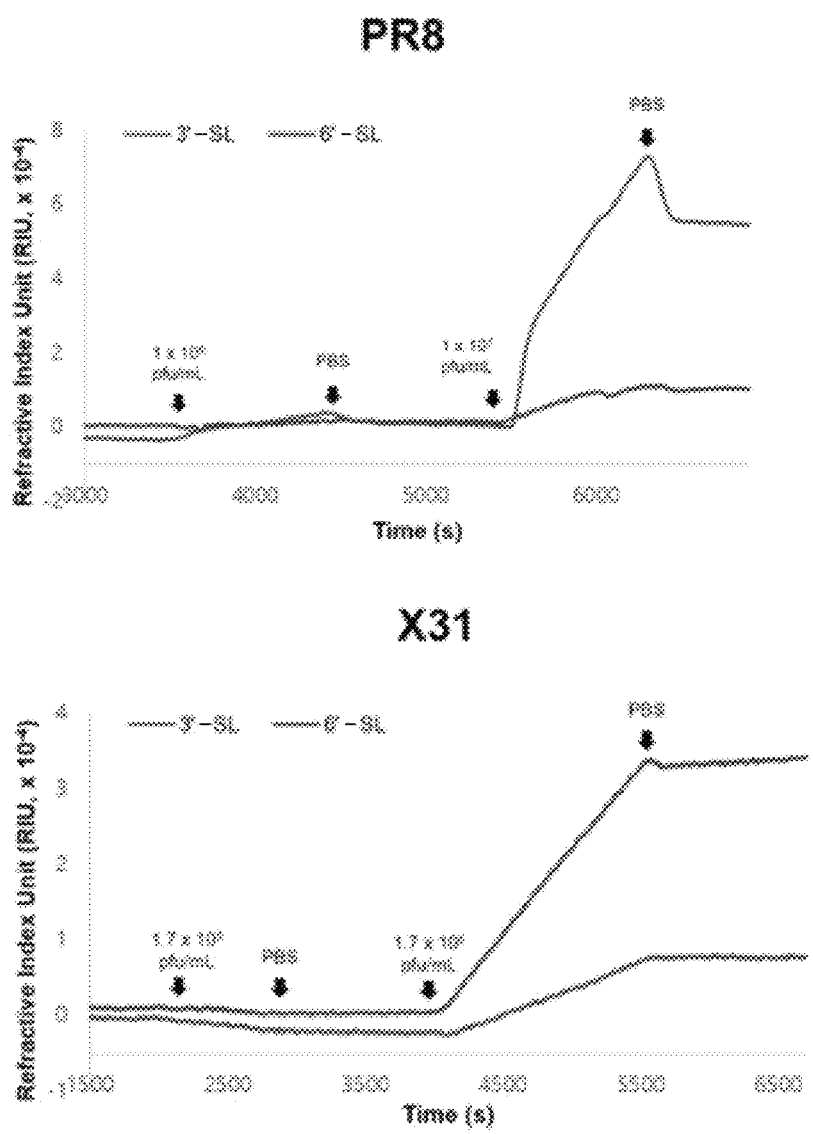
FIG. 11 illustrates the result of surface plasmon resonance (SPR) to determine the affinity to the virus strain of the nanodiscs (ND2,6SL; ND2,3SL) synthesized with the single-stranded viral receptor of the present invention.

Furthermore, an SPR binding assay was performed to determine the binding affinity of single-stranded viral receptors (3'-SL-M, 6'-SL-M) to X31 (H3N2) and PR8 (H1N1) virus strains (FIG. 11). As can be seen from FIG. 11, when 3'-sialyllactose (3'-SL) was used as a viral receptor, the binding affinity thereof to PR8 (H1N1) was excellent.

In addition, it can be seen that, when 6'-sialyllactose (6'-SL) was used as the viral receptor, the binding affinity to X-31 (H3N2) was excellent. This result is consistent with the result of the antiviral effect experiment.

Example 6: Preparation of Viral Receptor (SL-St) Using Thioether Bond

1) Introduction

The disulfide bond formed on cysteine used as an anchor using PDP-PE as in Example 4 may be disadvantageously cleaved under reduction conditions. This may affect the purification of the nanodisc. For this reason, an attempt was made to bind cysteine to the lipid using a more stable covalent bond.

Figure 12:
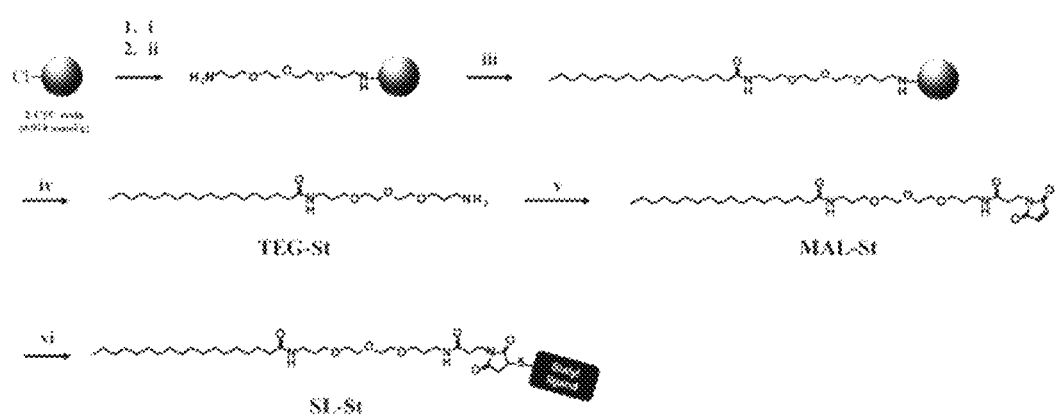
FIG. 12 is a schematic diagram illustrating a process of binding the single-stranded viral receptor (SL-M) or the multi-stranded viral receptor (SL-T) of the present invention to a maleimide lipid.

First, 4,7,10-trioxa-1,13-tridecanediamine (TEG) was bound to stearic acid (ST) through solid-phase synthesis, and N-succinimidyl 3-maleimidopropionate (NHS-MAL) was reacted with the amine group of TEG-ST to introduce maleimide thereinto to thereby synthesize a lipid (maleimide-TEG-St) having a maleimide functional group. Then, a thioether bond was formed through a reaction between the maleimide group of the lipid and the thiol group of the cysteine end of SL-M or SL-T to bind single- and multi-stranded viral receptors to lipids. A schematic diagram of this synthesis method is shown in FIG. 12.

2) Synthesis

A standard solid-phase synthesis method was used to introduce a maleimide group reactive to a thiol group to the end of stearic acid. Stearyl-TEG-CTC (St-TEG-CTC) was produced by binding stearic acid to the amine end group of 4,7,10-trioxa-1,13-tridecanediamine (TEG diamine) coupled to a 2-CTC resin using an amide production reaction. Specifically, the 2-CTC resin was treated with TEG diamine (40 eq.) and DIPEA (3 eq.) dissolved in dry DCM for 2 hours to load TEG diamine onto the resin.

After the reaction, the unbound reactive groups of the resin were end-capped with methanol for 30 minutes. Then, a coupling reaction was performed by adding stearic acid, DIC, and an NMP solution of HOBt (3 eq. of each with respect to the functional group of the resin) to the resin and shaking the mixture at room temperature. Coupling was identified by the Kaiser ninhydrin test.

After the synthesis was completed, St-TEG-NH2 was cleaved from the resin using a mixture solution of 95% TFA and 5% water for 2.5 hours.

Stearyl-maleimide (MAL-TEG-St) was synthesized by adding N-succinimidyl 3-maleimido propionate (BMPS) to stearyl-TEG amine (St-TEG-NH2). MAL-TEG-St and BMPS were dissolved in dry chloroform and mixed in a round-bottom flask. The mixture was incubated at room temperature with a magnetic stirrer for 3 hours. After the synthesis was completed, the product was purified by flash-column chromatography.

The viral receptor lipid (SL-St) of the present invention was synthesized through a maleimide-thiol reaction. The receptor (SL-M or SL-T) was dissolved in water and was added with methanol (water:methanol=1:4). MAL-TEG-St was dissolved in chloroform and was added with methanol (chloroform:methanol=1:4). The two solutions were mixed in a round-bottom flask and magnetically stirred overnight at room temperature. The progress of the reaction was monitored through TLC analysis.

3) Verification Using $^1$H-NMR Spectrum

Figure 13:
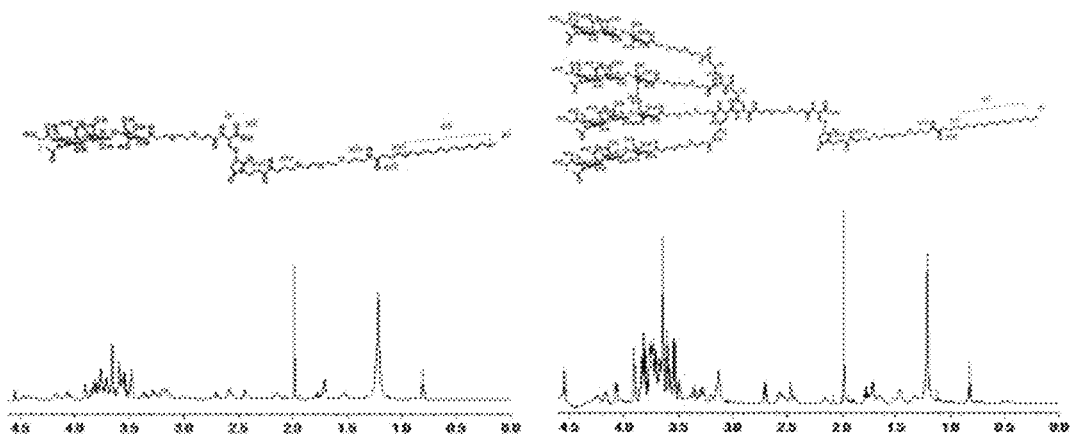
FIG. 13 illustrates the result of H-NMR analysis of the viral receptor lipid of the present invention.
Figure 14:
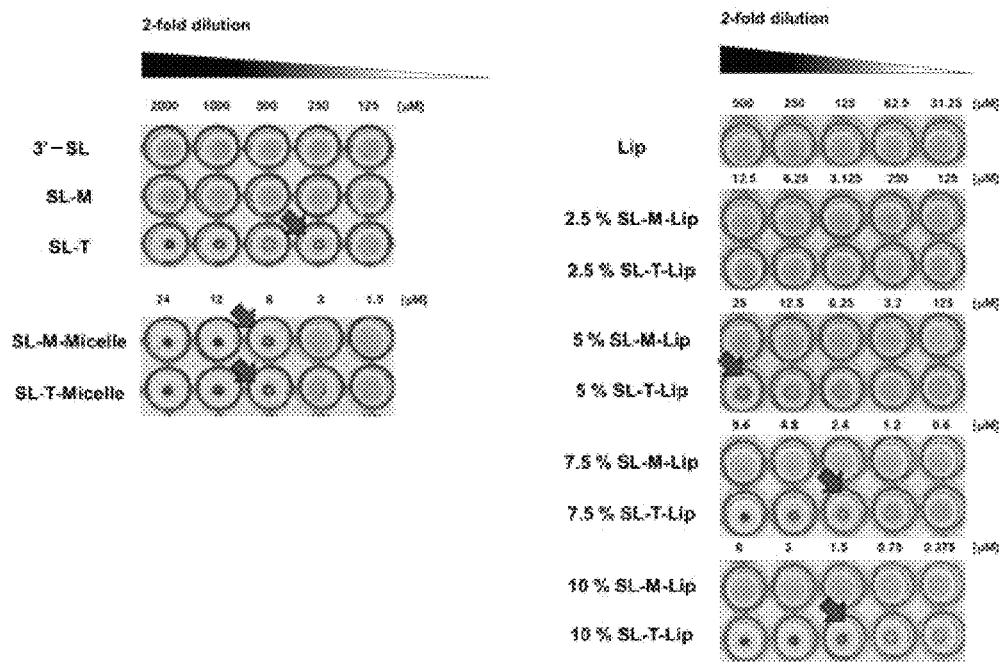
FIG. 14 illustrates the result of an HI assay to determine the virus-binding affinity of the viral receptor lipid of the present invention.
Figure 15:
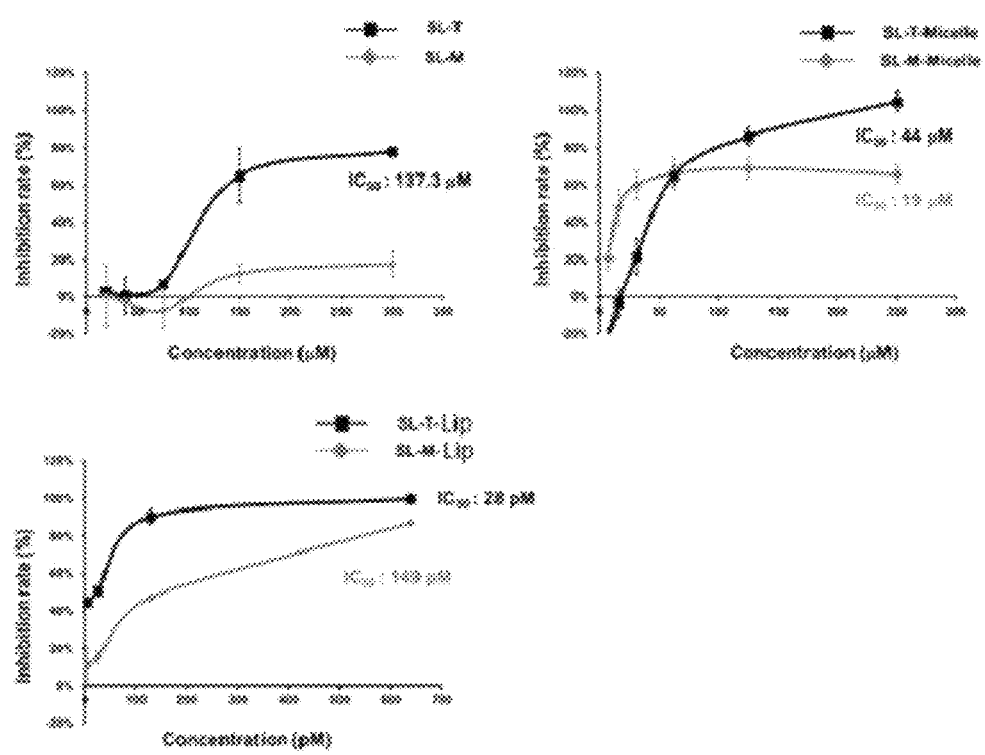
FIG. 15 illustrates the result of a MUNANA assay to determine inhibitory activity against a virus of the viral receptor lipid of the present invention.

The viral receptors (SL-M-St and SL-T-St) of the present invention were dissolved in a deuterium oxide (DO) solvent and analyzed using 700 MHz NMR (FIG. 13). The result of analysis showed that the viral receptor lipid (SL-St) of the present invention was successfully synthesized.

Example 7: Liposome Formation 1 Using Single-Stranded and Multi-Stranded Viral Receptor Lipids (SL-M-St and SL-T-St) According to Present Invention Prepared in Example 6

A spherical liposome, rather than a disc-shaped nanoperforator (nanodisc), was formed using the viral receptor lipids prepared in Example 6 (SL-M-St and SL-T-St; hereinafter, two types of viral receptor lipids, that is, single-stranded and multi-stranded viral receptor lipids, are collectively referred to as "SL-St").

1,2-Distearoyl-sn-glycero-3-phosphocholine (DSPC), the viral receptor lipid (SL-St) prepared in Example 6, and cholesterol were dissolved in chloroform. Then, cholesterol was added at 10 mol % to chloroform. The solution was dried in the presence of a stream of dry nitrogen gas until only a thin layer of lipid remained on the inner wall. The uncapped vials were placed in a vacuum desiccator for at least 3 hours to remove residual solvent therefrom. Then, the lipid mixture was hydrated with PBS (pH 7.4). The result was vortexed for a short time and then the resulting multilayered liposomes were sonicated using a probe sonicator for 3 cycles of 5 minutes each. Then, the liposome dispersion was extruded using a 0.45 mm syringe filter to obtain monolayer liposomes. The formation and size of liposomes were observed by DLS, and all liposomes were found to have a diameter of 120 to 150 nm.

Example 8: Experiment for Measuring Antiviral Effects of Micelles and Liposomes Using Viral Receptors and Viral Receptor Lipids (SL-St) of Present Invention 1) Hemagglutination Inhibition Assay (HI Assay)

First, the minimum virus concentration (1 HAU) at which cRBC does not precipitate was measured using chicken red blood cells (cRBC) known to bind to hemagglutinin of the virus and viruses (H1N2, H3N2). Upon exposure to a predetermined concentration or more of a virus, cRBC binds to the virus to produce a lattice (this phenomenon is referred to as "hemagglutination"), which inhibits clumping of cRBC. HI assay is an assay method capable of being used to evaluate how effectively a compound or substance to be analyzed binds with hemagglutinin of the virus and is widely used in influenza virus research. Here, the minimum concentration of an analyte sample at which cRBC is clumped and begins to precipitate in the form of red dots when observed above the plate is referred to as "KiHAI", and as KiHAI decreases, the effect of a virus inhibitor is considered to increase.

For HI assay, a virus with a concentration of 4 HAU was treated with each receptor, each receptor lipid, micelles composed of each receptor lipid, and liposomes containing each receptor, the result was added to cRBC, and then HI assay was performed. That is, 4HAU virus was treated with viral receptor lipids (SL-St; SL) synthesized using various concentrations of 3'-sialyllactose, single- and multi-stranded viral receptors (SL-M, SL-T), micelles (SL-M-micelles and SL-T-micelles) based on viral receptor lipids (SL-St; Sl-M-St and SL-T-St) synthesized using SL-M or SL-T, and SL-M-Lip or SL-T-Lip, which is a liposome prepared using the SL-M-St or SL-T-St viral receptor lipid, at 37° C. for 30 minutes. 50 μl of the treated mixture was mixed with 50 μl of cRBC, the resulting mixture was finally incubated at room temperature for 1 hour, and the concentration (KiHAI) at which cRBC started to precipitate in the form of red dots was observed (FIG. 14).

2) 4-Methylumbelliferyl-N-Acetyl-α-D-Neuraminic Acid-Based Microneutralization Assay (MUNANA Assay)

MUNANA assay is a method that evaluates how effectively infection with influenza virus and production of progeny virus are inhibited by measuring the activity of neuraminidase present on the surface of influenza virus.

MDCK II cells were prepared at $2\times10^5$ cells/mL in MEM (10% FBS, 100 U/mL of penicillin G, 100 μg/mL of streptomycin and 0.25 μg of amphotericin B) medium, seeded in an amount of 100 μL into each well of a 96-well plate, and incubated at 37° C. in the presence of 5% $CO_2$ one day before infection. On the day of infection, viral receptor lipids (SL-M-St or SL-T-St), micelles produced using the viral receptor lipids (SL-M-St or SL-T-St) and liposomes (SL-M-Lip or SL-T-Lip) produced using the viral receptor lipids (SL-M-St or SL-T-St) were prepared by 2× serial dilution. These serial dilutions (5 μL) were mixed with IAV in infection medium (195 μL of MEM using 1% antibiotic) (at IAV final concentration of $2\times10^4$ pfu/mL) and incubated at 37° C. in 5% $CO_2$ for 1 hour.

The cells were washed twice with PBS, and pretreated or intact virus (MOI of 0.2) was added to the infection medium (200 μl) and then incubated at 37° C. in the presence of 5% $CO_2$ for 24 hours.

50 μL of a 4-MUNANA (4-methylumbelliferyl-N-acetyl-α-D-neuraminic acid) solution (150 μM) in PBS was added to each well, followed by further incubation at 37° C. for 2 hours. Finally, fluorescence (excitation: 355 nm) at 460 nm was measured using a Synergy H1 (BioTek) (FIG. 15).

3) Results Analysis

HI analysis data (FIG. 14) shows that 3'-sialyllactose (3'-SL) and 3'-SL-M did not inhibit hemagglutination even at 2 mM, the highest concentration used. Meanwhile, the multi-stranded receptor SL-T had a KiHAI of 250 μM for PR8 virus, which indicates that the multi-stranded receptor was more efficient as a virus inhibitor. SL-M-St and SL-T-St, in which a stearyl group is bound to the SL-M and SL-T receptors, respectively, produce micelles in an aqueous solution. The micelle was referred to as "SL-M-micelle" or "SL-T-micelle" and each had a KiHAI of about 6 μM. These results indicate that inhibitory activity can be improved by more than 40 times as each receptor is self-assembled to form a nanostructure and provide a multivalent effect. Liposomes (SL-M-Lip) containing SL-M-St did not inhibit hemagglutination within the tested concentration range when SL-M-St was contained in an amount of 2.5 to 10 mol %. Meanwhile, liposomes (SL-T-Lip) containing the multi-stranded receptor lipid, SL-T-St, had a KiHAI of 1.5 to 25 μM when SL-T-St was contained in an amount of 5 to 10 mol %. Overall, these results indicate that the multi-stranded multivalent effect for the receptor plays a key role in improving inhibitory activity, and when a plurality of receptor molecules is self-assembled, both single-stranded and multi-stranded receptors exert maximum multivalent effects. Liposomes introduced with the multi-stranded receptor exhibited greatly improved inhibitory activity when the receptor was present on the surface, and the inhibitory activity against the virus could be further improved by controlling the composition ratio in the liposome. This clearly demonstrated that the SL-T receptor itself and the nanomaterials (micelles, liposomes) prepared using SL-M or SL-T had virus-binding affinity.

The result of the inhibition assay using MUNANA at MDCK (MOI=0.2) in addition to HI analysis (FIG. 15) showed that the single-stranded receptor SL-M exhibited inhibition of 12% at 150 μM, and no further effects were observed even at higher concentrations. Meanwhile, the multi-stranded receptor SL-T exhibited inhibition of 78% at 300 μM. In particular, 150 μM SL-T exhibited inhibition of 65%, which was about 5 times higher than the inhibition of 12% of SL-M. Therefore, the antiviral effect of SL-T was 4 times higher than that of SL-T due to the multivalent binding affinity thereof. SL-T had an $IC_{50}$ of 137.3 μM. Micelles (SL-M-Micelle and SL-T-Micelle) containing viral receptor lipids (SL-M-St and SL-T-St) had $IC_{50}$ of 19 μM and 44 μM, respectively. This means that a plurality of viral receptor lipid molecules is self-assembled to form micelles, whereby viral inhibitory activity can be greatly improved due to the multivalent effect. SL-M-Lip and SL-T-Lip, which are liposomes containing viral receptor lipids, had $IC_{50}$ of 149 μM and 44 μM, respectively, and the multi-stranded receptor, when present on the liposome surface, exhibited improved influenza virus (PR8) inhibitory activity and had potential antiviral activity.

Example 9: Liposome Formation 2 Using Viral Receptor Lipid (SL-ST)

Each of the viral receptor lipids (SL-M-St, SL-T-St) was mixed with 1,2-distearoyl-sn-glycero-3-phosphocholine (DSPC) at molar ratios of 2.5%, 5% and 7.5% to form 6 types of liposomes containing single- and multi-stranded receptors. The formation and size of liposomes were observed through DLS and all liposomes were found to have a diameter of 65 to 75 nm. The other details for preparation of liposomes were the same as in the method described in Example 7.

Example 10: Experiment 2 for Measuring Antiviral Effect of Liposomes Using Viral Receptor Lipids (SL-ST)

HI assay and MUNANA assay according to Example 8 were performed using the viral receptor lipid (SL-ST) and liposomes using the viral receptor lipid (SL-ST) according to Example 9 and a control group, and the results shown in Table 1 below were obtained.

TABLE 1

Results of HI assay and MUNANA assay

| Molar ratio of receptor lipid (SL-St) | | HI assay | | MUNANA assay | |
|---|---|---|---|---|---|
| | | $K_I^{HAI}{}_{tot}$* (μM) | $K_I^{HAI}{}_{receptor}$** (μM) | $IC_{50\ tot}$ (μM) | $IC_{50\ receptor}$ (μM) |
| 0% | | N/A | N/A | N/A | N/A |
| 2.5% | M | N/A | N/A | 104 | 2.6 |
| | T | N/A | N/A | 19.2 | 0.48 |
| 5% | M | N/A | N/A | 26 | 1.3 |
| | T | 500 | 25 | 9.2 | 0.46 |
| 7.5% | M | N/A | N/A | 21.2 | 1.59 |
| | T | 32 | 2.4 | 3.6 | 0.27 |

*tot: concentration of liposome
**receptor: concentration of receptor

As can be seen from Table 1, the multiple-stranded receptor exhibited a higher inhibitory effect on the influenza virus than the single-stranded receptor and as the replacement ratio of the viral receptor lipid with respect to DSPC increased, the inhibitory effect on the influenza virus was increased. In addition, it can also be seen that when the liposome had a smaller size (65-75 nm) than the size (120-150 nm) of the liposome prepared in Example 8, a liposome containing the single-stranded receptor (SL-M-Lip) also exhibited inhibitory activity on the virus (PR8). It can also be seen that the small size of the liposome can increase the contact area with the virus.

Example 11: Linker Containing Aminooxy Group and Synthesis of Viral Receptor Using the Same 1) Introduction
The single- and multi-stranded linkers, which are intermediates of Example 1, have an amine group as a functional end group binding to sialyllactose, and had a problem in that the step of binding to sialyllactose took a long time (about 2 weeks). For this reason, an attempt was made to shorten the time of the lactose-coupling step. In addition, the single- and multi-stranded linkers as intermediates of Example 1 had secondary amines left after the sialyllactose-coupling step, and thus were positively charged. For this reason, an attempt was made to improve affinity for viruses and the inhibitory ability thereon by controlling this charge characteristic.

For this purpose, (boc-aminooxy)acetic acid was coupled to a multi-stranded linker having an amine end group in the solid-phase synthesis process, followed by deprotection, to synthesize a multi-stranded linker having an aminooxy end group, and then each multi-stranded linker was cleaved from the resin in the presence of an acid. After HPLC purification, a product having a yield of 90% and a purity of 95% or more was obtained as a result.

2) Synthesis of Linker Containing Aminooxy Group and Viral Receptor Using the Same
After solid-phase synthesis of the multi-stranded linker, 2-aminooxyacetic acid was further coupled to the N-terminus in a solid phase through an amide bond using DIC and HOBt.

After complete resin-phase synthesis, multi-stranded aminooxy linkers were prepared using a mixture solution of 82.5% TFA, 5% water, 5% phenol, 5% thioanisole and 2.5% 1,2-ethanedithiol at room temperature for 2 hours, and were cleaved from the resin. After removing the solvent using a rotary evaporator, the crude product was precipitated with ice-cold diethyl ether (30 times in volume) to collect the crude product and thereby obtain a white solid. The multi-stranded aminooxy linker was further purified to a purity higher than 95% using semi-prep HPLC.

In order to prepare an aminooxy viral receptor by binding sialyllactose to the linker through an oxime bond, the sialyllactose was reacted with the linker in the presence of an anhydrous methanol solvent at 50° C. for 3 days with magnetic stirring (400 rpm).

Figure 16:
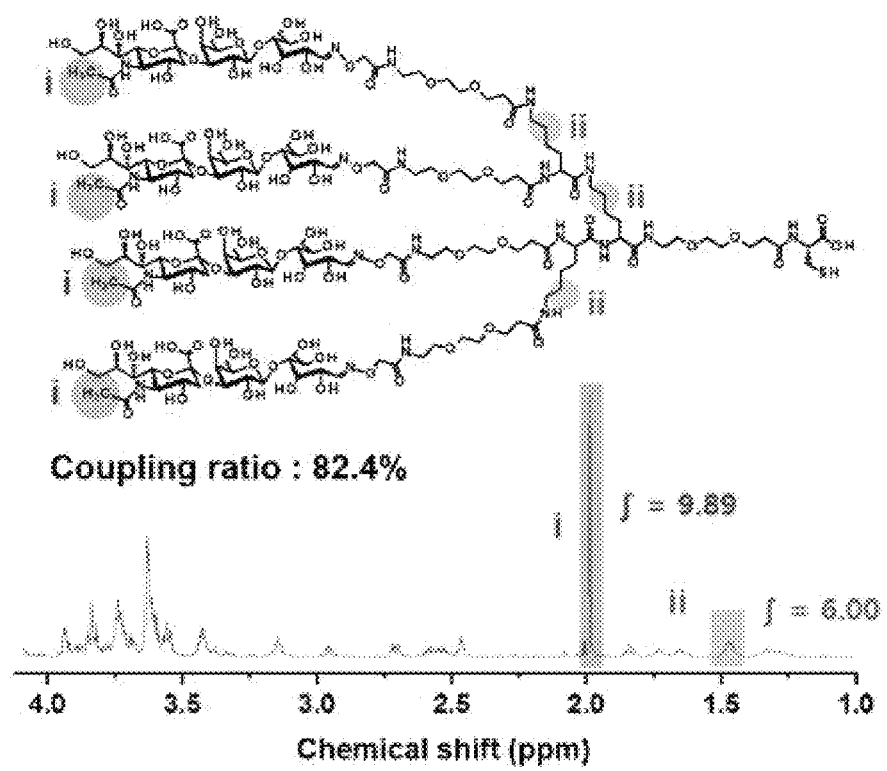
FIG. 16 illustrates the result of H-NMR analysis of an oxime-bond-based viral receptor bound with 3'-sialyllactose.
Figure 17:
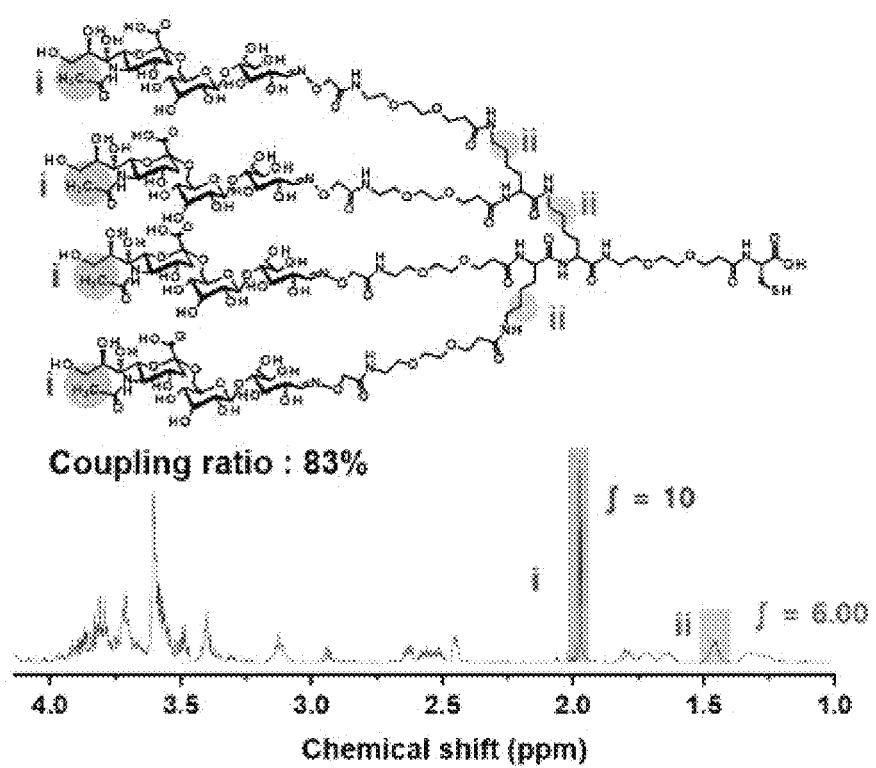
FIG. 17 illustrates the result of H-NMR analysis of an oxime-bond-based viral receptor bound with 6'-sialyllactose.

3) $^1$H-NMR Analysis
The sample was dissolved in a deuterium oxide (D2O) solvent, and the $^1$H-NMR spectrum of the aminooxy receptor was analyzed using 700 MHz NMR. The amount of SL bound to the linker was calculated through the data analysis. The amount was obtained by comparing 1.45 ppm of the delta carbon of the linker with 2.07 ppm of the acetyl group of SL (FIGS. 16 and 17). FIG. 16 illustrates a coupling ratio of 82.4%, obtained as a result of $^1$H-NMR analysis of an oxime binding-based multi-stranded receptor to which 3'-sialyllactose is bound. FIG. 17 illustrates a coupling ratio of 83%, obtained as a result of H-NMR analysis of an oxime binding-based multi-stranded receptor to which 6'-sialyllactose is bound.

Figure 18:
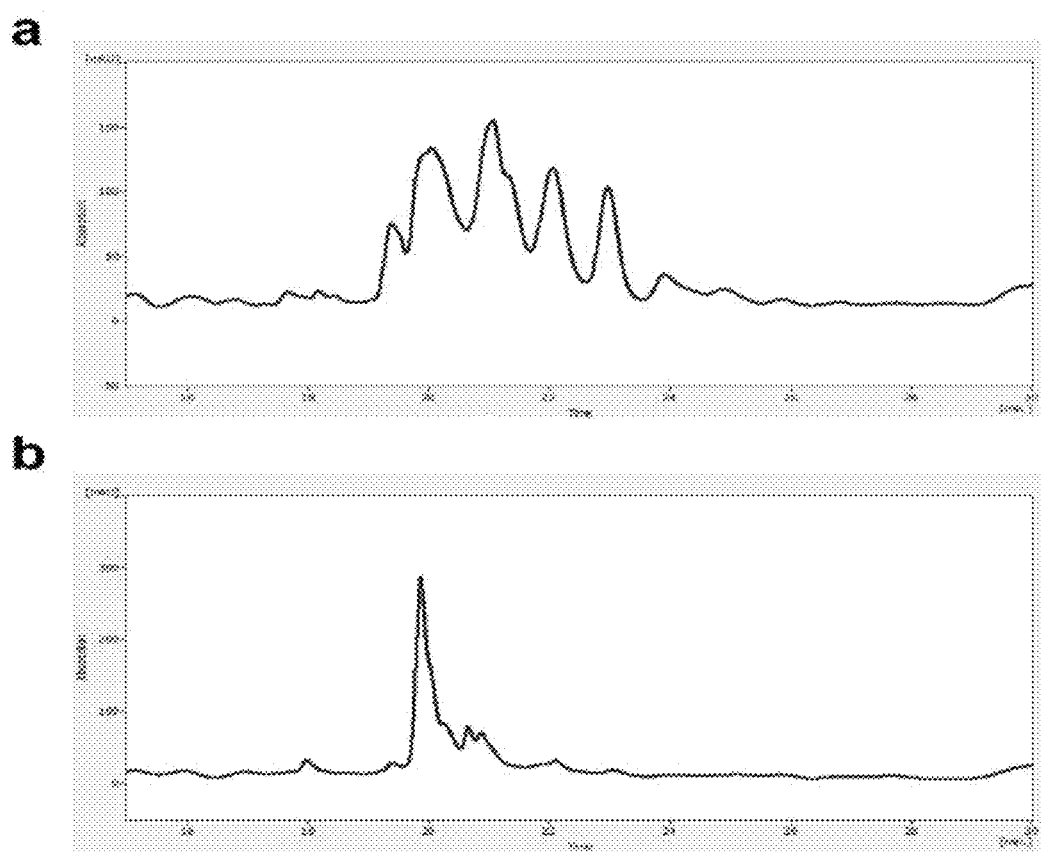
FIG. 18 illustrates the result of HPLC analysis of the oxime-bond-based viral receptor under different reaction conditions ((a) pH 4.6 acetate buffer, (b) methanol, 0.1% acetic acid) so as to optimize the binding conditions of the oxime-bond-based viral receptor.

4) Search for Optimal Conditions for Oxime Reaction
In order to determine the optimal conditions for the oxime bond between the aminooxy linker and sialyllactose, the reaction was performed under the following reaction conditions ((a) pH 4.6 acetate buffer, (b) methanol, 0.1% acetic acid). 24 hours after the start of the reaction, TLC analysis and iodine staining were performed. As a result, the aminooxy multi-stranded linker was found to be consumed in both (a) and (b). However, the difference in reaction time between the two conditions could not be determined. Then, the reaction progress was monitored through TLC (Silica gel 60G F254; EtOH:DI water=2:1) and HPLC analysis (FIG. 18).

It can be seen that as the conjugation ratio of sialyl lactose to the aminooxy multi-stranded linker increased, the retention time of the corresponding peak on the HPLC chromatogram decreased. In addition, it can be seen from FIG. 18 that the retention time of the receptor peak generated in the methanol solvent was shorter overall than that in the acetate buffer solvent. That is, it can be seen that the reaction rate and efficiency in the methanol solvent were higher.

Figure 19:
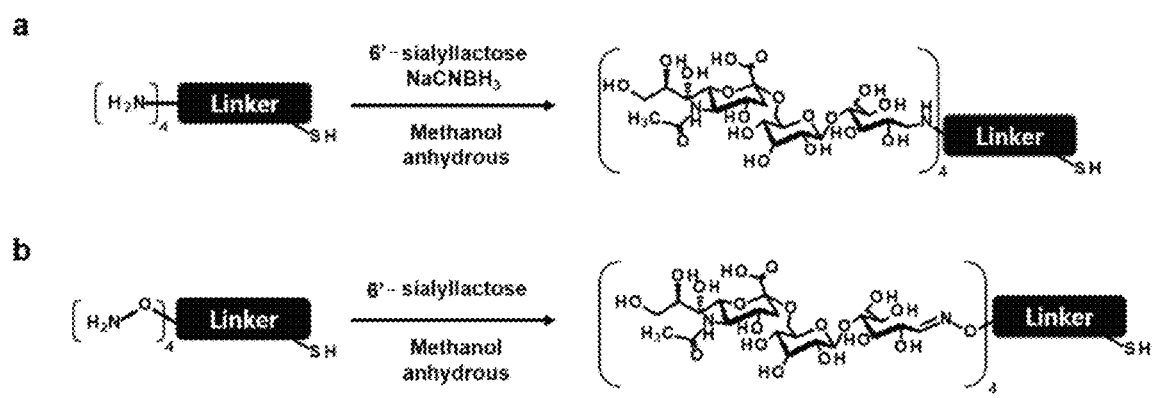
FIG. 19 is a schematic diagram illustrating a process of synthesizing a sialyllactose-bound viral receptor using an amine or aminooxy end of a linker after optimization of reaction conditions.

5) Production of Multi-Stranded Linker (Amine End, Aminooxy End)-Based Viral Receptors In order to improve the reaction efficiency and shorten the reaction time of the conventional reductive amination (pH 8.7 borate buffer, borane-pyridine complex (BPC)) step in the amine end group-containing multi-stranded linker-based receptor synthesis method according to Example 1, reaction was performed using anhydrous methanol, as a solvent, instead of a buffer and sodium cyanoborohydride (NaCNBH$_3$), as a reductant, instead of BPC which has a side effect of causing a reduction reaction on the reducing end of sialyllactose. Then, a comparative experiment was conducted. A schematic diagram associated with a synthesis method thereof is shown in FIG. 19.

The result of the experiment showed that, in the aminooxy end group-containing linker, the aminooxy group reacted with the reducing end of sialyllactose without the aid of a reductant to produce an oxime bond. In addition, unlike the amino end group-containing linker, the aminooxy end group-containing linker had no charge at the binding site.

Example 12: Synthesis of Multi-Stranded Aminooxy Viral Receptor Lipids

Figure 20:
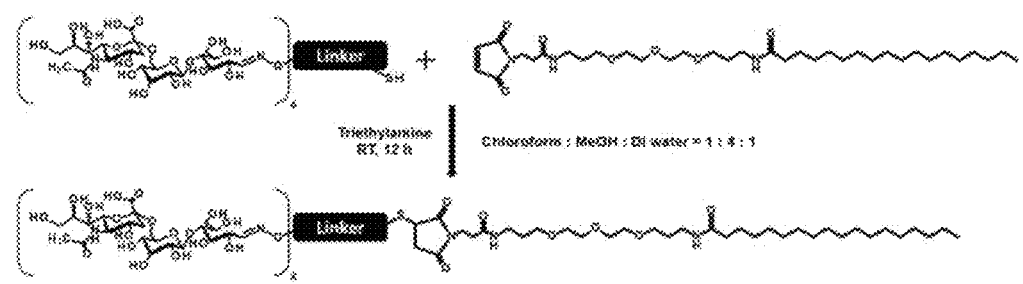
FIG. 20 is a schematic diagram illustrating the process of synthesizing a multi-stranded aminooxy-based viral receptor lipid.

The synthesized multi-stranded aminooxy receptor was reacted with a lipid containing a maleimide group at one end (MAL-TEG-St) to synthesize a lipidized viral receptor through a maleimide-thiol reaction. The reaction was performed in a co-solvent of organic solvent/aqueous solution (DI water:methanol:chloroform=1:4:1), and the pH was adjusted by adding triethylamine thereto to promote the thiol-maleimide reaction. Synthesis was possible through a coupling reaction for 12 hours. A schematic diagram associated with the synthesis process is shown in FIG. 20. Then, HPLC purification was performed. After purification, the multi-stranded aminooxy viral receptor lipid containing 3'- and 6'-sialyllactose was identified through $^1$H-NMR analysis (FIGS. 21 and 22).

Figure 21:
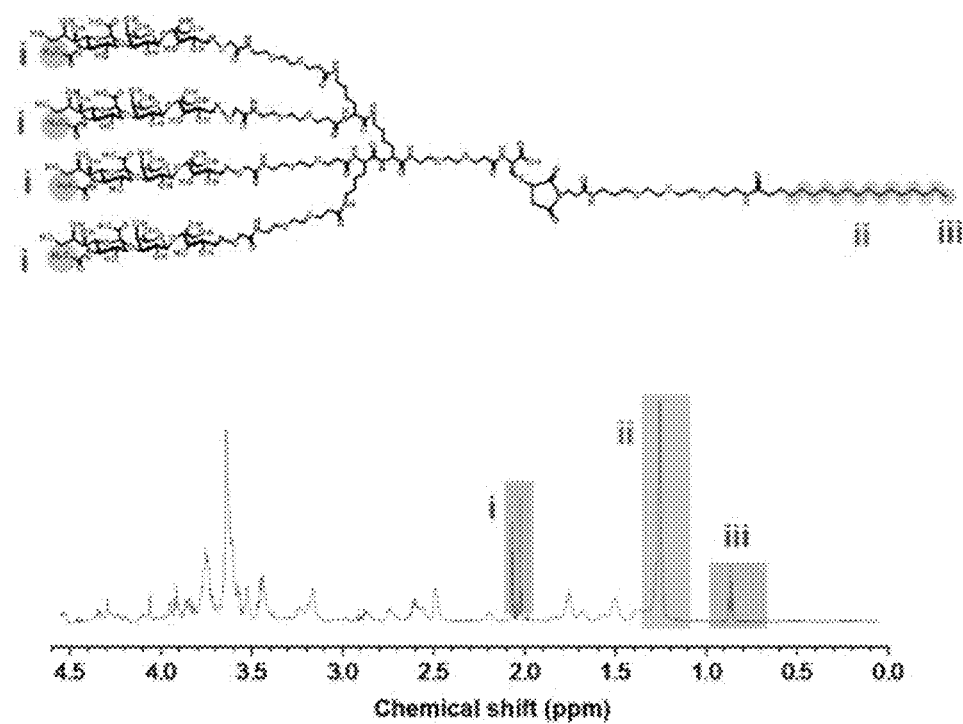
FIG. 21 illustrates the result of $^1$H-NMR analysis of the oxime-bond-based multi-stranded viral receptor lipid containing 3'-sialyllactose.
Figure 22:
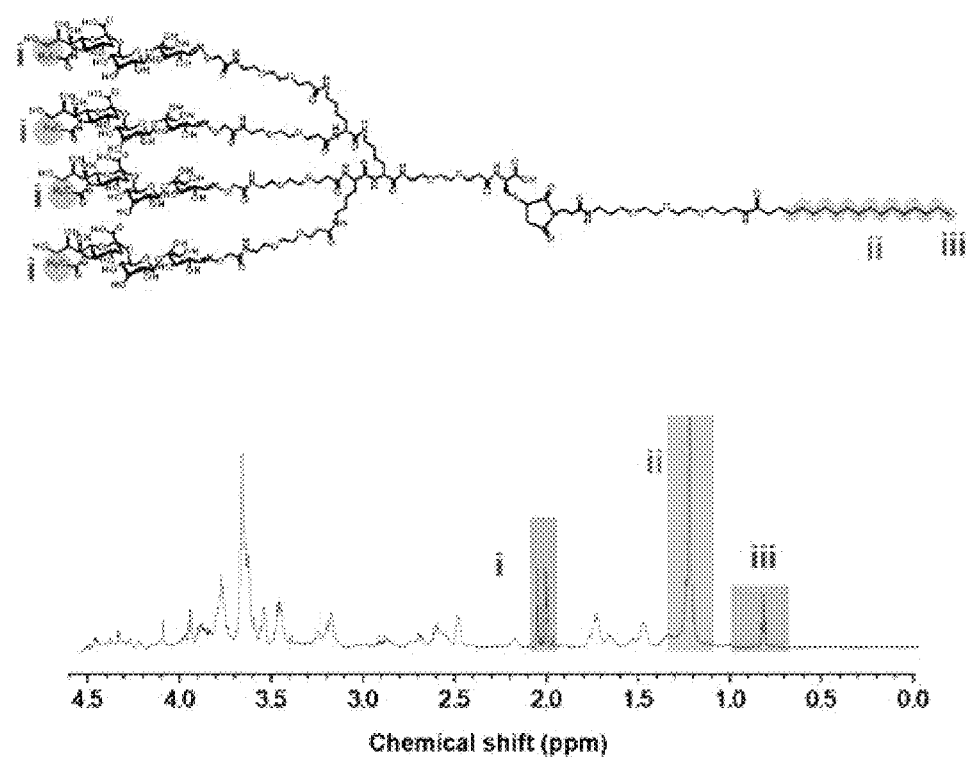
FIG. 22 illustrates the result of $^1$H-NMR analysis of the oxime-bond-based multi-stranded viral receptor lipid containing 6'-sialyllactose.

FIG. 21 illustrates an oxime-bond-based multi-stranded receptor lipid containing 3'-sialyllactose, and FIG. 22 illustrates an oxime-bond-based multi-stranded receptor lipid containing 6'-sialyllactose, wherein i represents 3H of an N-acetyl group (CH$_3$) in sialic acid, ii represents 28H in stearic acid, and iii represents 3H of a CH$_3$ end in stearic acid.

Figure 23:
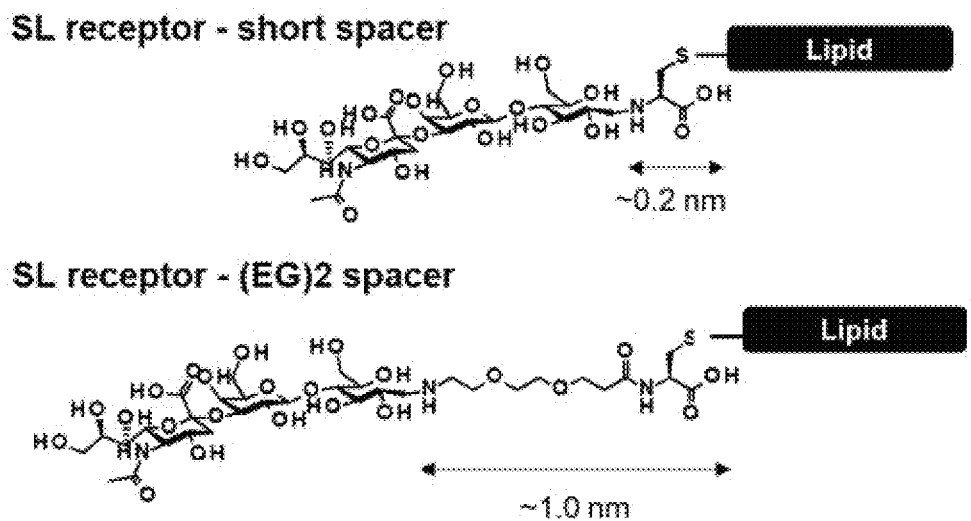
FIG. 23 illustrates the length of the spacer used to compare the effect according to the length of the spacer used in the viral receptor lipid according to the present invention.

Example 13: Comparative Evaluation of Inhibitory Activity Against Virus Depending on Length of Spacer of Viral Receptor The PR8 virus inhibitory activity of SL liposomes (SL-Lip) depending on the length of the spacer of the viral receptor was compared. Ganglioside GM3 containing no spacer, a viral receptor containing only cysteine (anchor), and a receptor containing a spacer of (EG)2Cys were prepared (FIG. 23), and then liposomes introduced with each receptor were prepared (10 mol % of viral receptor in liposomes). Under the same conditions, PR8 virus (H1N1) and each receptor-liposome were incubated for 30 minutes and then inoculated into MDCK cells and cultured for 16 hours. The produced progeny virus was quantified by MUNANA assay, which is a method for measuring neuraminidase activity (FIG. 24).

Figure 24:
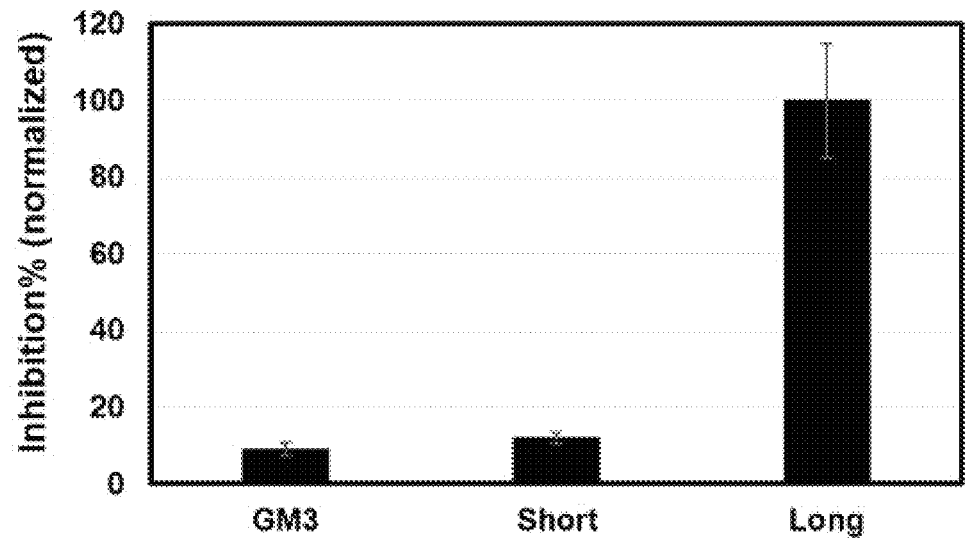
FIG. 24 illustrates the binding affinity to a viral surface protein (hemagglutinin) depending on the presence or absence of the spacer used in the viral receptor lipid and the difference in length of the spacer.

As can be seen from FIG. 24, the liposome introduced with the SL-(EG)2Cys viral receptor having a relatively long spacer (1 nm in length) exhibited virus inhibitory activity 8.5 times and 11.1 times higher than those of a liposome having a short spacer (0.2 nm in length) and GM3-liposome having no spacer. This demonstrated that the binding affinity with the virus surface protein (hemagglutinin) varies depending on the presence or absence of the spacer and the length of the spacer.

As is apparent from the foregoing, the viral receptor of the present invention has excellent virus-binding affinity and can be used to develop a drug capable of effectively inhibiting a virus.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. A viral receptor comprising a sialic acid compound and a spacer linking to the sialic acid compound,
   wherein the sialic acid compound comprises sialic acid linking to galactose and glucose, and
   the spacer is a polymer having an amine group (—NH$_2$) or an aminooxy group (NH$_2$—O—) at one end thereof and a carboxyl group (—COOH) capable of linking to a lipid at a remaining end thereof,
   wherein the spacer is selected from a plurality of spacers linking to one another via lysine to form a spacer complex.

2. The viral receptor according to claim 1, wherein the viral receptor is further linking to an anchor, which is a compound that has a functional group capable of linking to the carboxyl end group (—COOH) of the spacer at one end thereof and another functional group capable of binding to the lipid at a remaining end thereof.

3. The viral receptor according to claim 2, wherein the another functional group capable of linking to the lipid is a thiol group.

4. The viral receptor according to claim 2, wherein the lipid is selected from the group consisting of phospholipid and fatty acid.

5. The viral receptor according to claim 1, wherein the sialic acid compound is linked to the spacer by forming a secondary amine bond through reaction of an aldehyde group of the glucose in the sialic acid compound with the amine group of the spacer, or by forming an oxime bond through reaction of the aldehyde group of the glucose in the sialic acid compound with the aminooxy group (NH$_2$—O—) of the spacer.

6. The viral receptor according to claim 1, wherein the sialic acid compound comprises sialic acid linking to an oligosaccharide including a plurality of repeating units, each including a disaccharide in which galactose is linking to glucose.

7. The viral receptor according to claim 1, wherein the sialic acid compound is sialyllactose.

8. The viral receptor according to claim 7, wherein the sialyllactose is 3'-sialyllactose or 6'-sialyllactose.

9. The viral receptor according to claim 1, wherein the lipid has any one functional group selected from a maleimide group (H$_2$C$_2$(CO)$_2$N—), a pyridyl disulfide group (Py- S—S—), a haloacetyl group (X—CH$_2$—CO—), an acryloyl group (H$_2$C=CH—CO—), and a vinyl group (H$_2$C=CR—).

* * * * *